US006982172B2

(12) United States Patent
Yang et al.

(10) Patent No.: US 6,982,172 B2
(45) Date of Patent: Jan. 3, 2006

(54) OOCYTE VITRIFICATION TECHNIQUE

(75) Inventors: Xiangzhong Yang, Storrs, CT (US); Andras Dinnyes, Budapest (HU)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 09/755,205

(22) Filed: Jan. 4, 2001

(65) Prior Publication Data

US 2002/0009704 A1 Jan. 24, 2002

Related U.S. Application Data

(60) Provisional application No. 60/215,433, filed on Jun. 30, 2000, provisional application No. 60/174,383, filed on Jan. 4, 2000, and provisional application No. 60/174,424, filed on Jan. 4, 2000.

(51) Int. Cl.
*A01N 1/02* (2006.01)
*C12N 5/06* (2006.01)

(52) U.S. Cl. .......................... 435/374; 435/1.3; 435/2; 435/375

(58) Field of Classification Search ................ 435/260, 435/374, 2, 307.1, 200, 375, 1.3
See application file for complete search history.

(56) References Cited

U.S. PATENT DOCUMENTS

| 4,865,871 A | 9/1989 | Livesey et al. |
|---|---|---|
| 5,171,660 A | 12/1992 | Carpenter et al. |
| 5,780,295 A | 7/1998 | Livesey et al. |
| 5,817,453 A | 10/1998 | Brinster |
| 5,945,577 A | 8/1999 | Stice et al. |
| 6,011,197 A | 1/2000 | Streichenko et al. |

FOREIGN PATENT DOCUMENTS

WO  WO 99/66271  * 12/1999

OTHER PUBLICATIONS

Arav et al. Journal of Reproduction and Fertility. 1993, 99: 353–358.*
Steponkus, P.L. et al., Cryopreservation of *Drosophila melangaster* Embryos, Nature, May 10, 1990, vol. 45, pp. 170–172, especially materials and methods sections.
Mazur, P. et al., Contributions of Cooling and Warming Rate and Developmental Stage to the Survival of *Drosphila* Embryos cooled to 205C, Cryobiology, Feb. 1993, vol. 3, No. 1, pp. 45–73, summarized in abstract.
J. Carroll, et al., Increase in Digyny Explains Polyploidy After In–Vitro Fertilization Of Frozen–Thawed Mouse Oocytes, Journal Of Reproduction And Fertility, vol. 85, 1989, pp 489–494.

C. Vincent, et al., The Hardening Effect Of Dimethylsulphoxide On The Mouse Zona Pellucida Requires The Presence Of An Oocyte And Is Associated With A Reduction In The Number Of Cortical Granules Present, Journal Of Reproduction And Fertility, vol. 89, 1990, pp. 253–259.
Zishu Liu, et al., Development of Bovine Embryos In KSOM With Added Superoxide Dismutase And Taurine And With Five And Twenty Percent $O_2^1$, Biology Of Reproduction, vol. 53, 1995, pp 786–790.
Alex Martino, et al., Effect Of Chilling Bovine Oocytes On Their Developmental Competence, Molecular Reproduction And Development, vol. 45, 1996, pp. 503–512.
Rebecca R. Aman, et al., Effects Of Cooling and Rewarming On The Meiotic Spindle And Chromosomes Of In Vitro–Matured Bovine Oocytes, Biology Of Reproduction, vol. 50, 1994, pp 103–110.
K. Schellander, et al., Effects Of Different Cryoprotectants And Carbohydrates On Freezing Of Matured And Unmatured Bovine Oocytes, Theriogenology, vol. 42, 1994, pp 909–915.
J.M. Lim, et al., Developmental Competence Of Bovine oocytes Frozen At Various Maturation Stages Followed By In Vitro Maturation And Fertilization, vol. 37 No. 2, Feb. 1992, pp. 351–361.
W.F. Rall, et al., High In Vitro And In Vivo Survival Of Day 3 Mouse Embryos Vitrified Or Frozen In A Non–Toxic Solution Of Glycerol And Albumin, Journal Of Reproduction And Fertility, vol. 101, 1994, pp. 681–688.
J.M. Lim, et al., The Post–Thaw Developmental Capacity Of Frozen Bovine Oocytes Following In Vitro Maturation And Fertilization, Theriogenology, vol. 35, 1991, pp. 1225–1235.
T. Otoi, et al., Developmental Capacity Of Bovine Oocytes Frozen In Different Cryoprotectants, Theriogenology, vol. 40, 1993, pp. 801–807.
Martino, A., Development Into Blastocysts Of Bovine Oocytes Cryopreserved By Ultra–Rapid Cooling, Biology Of Reproduction, vol. 54, 1996, pp. 1059–1069.
G. Vajta, Open Pulled Straw (OPS) Vitrification: A New Way To Reduce Cryoinjuries Of Bovine Ova And Embryos, Molecular Reproduction And Development, vol. 51, 1998, pp 53–58.
Kazumi Ito, et al., Effects of Timing Of Oocyte Cryopreservation On In Vitro Development Of Nuclear–Transferred Bovine Zygotes, Molecular Reproduction And Development, vol. 54, 1999, pp. 81–85.
Peter Freistedt, et al., Energy Status Of Nonmatured And In Vitro–Matured Domestic Cat Oocytes And Of Different Stages Of In Vitro–Produced Embryos: Enzymatic Removal Of The Zona Pellucida Increases Adenoisine Triphosphate Content And Total Cell Number Of Blastocysts, Biology Of Reproduction, vol. 65, 2001, pp. 793–798.

(Continued)

*Primary Examiner*—Vera Afremova
(74) *Attorney, Agent, or Firm*—Edwards & Angell, LLP

(57) ABSTRACT

A new method of cryopreservation based on the very fast cooling rates achieved by the direct contact of small droplets of vitrification solution containing biological sample with a very cold solid surface.

17 Claims, 1 Drawing Sheet

OTHER PUBLICATIONS

Andras Dinnyes, et al., Timing Of The First Cleavage Post–Insemination Affects Cryosurvival Of In Vitro–Produced Bovine Blastocysts, Molecular Reproduction And Development, vol. 53, 1999, pp. 318–324.

Lin Liu, et al., Parthenogenetic Development And Protein patters Of Newly Matured Bovine Oocytes After Chemical Activation, Molecular Reproduction And Development, vol. 49, 1998, pp. 298–307.

Chikara Kubota, et al., In Vitro And In Vivo survivial Of Frozen–Thawed Bovine Oocytes After IVF, Nuclear Transfer, And Parthenogenetic Activation, Molecular Reproduction And Development, vol. 51, 1998, pp. 281–286.

S. Saha, et al., Normal Calves Obtained After Direct Transfer Of Vitrified Bovine Embryos Using Ethylene Glycol, Trehalose, and Polyvinylpyrrolidone, Cryobiology, vol. 33, 1996, pp. 291–299.

T. Otoi, et al., Cryopreservation Of Mature Bovine Oocytes By Vitrification In Straws, Cryobiology, vol. 37, 1998, pp. 77–85.

T. Suzuki, et al., Fertilization And Development Of Frozen–Thawed Germinal Vesicle Bovine oocytes By A One–Step Dilution Method In Vitro, Cryobiology, vol. 33, 1996, pp. 515–524.

B.S. Yang, et al., Viability Of In Vitro–Derived Bovine Zygotes Cryopreserved In Microdrops, Theriogenology, vol. 51, 1999, p. 178.

K. Papis, et al., The Effect of Gentle Pre–Equilibration On Survival And Development Rates Of Bovine In Vitro Matured Oocytes Vitrified In Droplets, Theriogenology, vol. 51, 1999, p. 173.

M. Lane, et al., Live Births Following Vitrification Of hamster Embryos Using A Novel Containerless Technique, Theriogenology, vol. 51, 1999, p. 167.

T.T. Peura, et al., Vitrification Of Bovine Cytoplasts For Nuclear Transfer, Theriogenology, vol. 51, 1999, p. 211(abstract).

Dinnyes, A. et al: "High development rates of vitrified bovine occytes following parthenogenetic activation, in vitro fertilization, and somatic cell nuclear transfer" Biology of Reproduction, vol. 63, Mar. 2000.

Otoi, T. et al: "Cryopreservation of Mature Bovine Oocytes By Vitrification in Straws", Cryobiology, Academic Press Inc., vol. 37, No. 1, Aug. 1998, pp 77–85.

* cited by examiner

OOCYTE VITRIFICATION TECHNIQUE

RELATED ART

This application claims priority from U.S. Provisional Patent Applications Nos. 60/174,383 and 60/174,424, both filed Jan. 4, 2000, and U.S. Provisional Patent Application No. 60/215,433, filed Jun. 30, 2000, the disclosures of which are incorporated by reference in their entirety herein.

BACKGROUND OF THE INVENTION

1. Field of the Invention

The present invention generally relates to a method for the cryopreservation of biological samples. More particularly, the present invention relates to a method for the cryopreservation of biological samples in solution based on very fast cooling rates achievable by contacting small droplets of the solution on a very cold solid surface. The cryopreservation method has been found to be particularly useful in the cryopreservation of oocytes and embryos, in particular mammalian embryos.

2. Background of Related Art

It is frequently the case that one desires to maintain biological samples for long periods of time, for example when the sample is desired to be used for a particular purpose at a later time. Unfortunately, as recognized by those of ordinary skill in the art, the freezing, cryopreservation and thawing, of biological samples using presently available techniques often is less than optimal, as biological activity of the biological sample is often significantly diminished. As the practical use of certain biological techniques dictates certain cells be stored for long periods of time, there has been a growing demand for new method of preserving biological samples, in particular cellular material, such the biological functionality of the material is preserved after warming. A particular need for the preservation of biological materials has arisen in germ plasma, in vitro embryo production and nuclear transfer.

There has been an increasing effort to store the oocytes and embryos of many animal species. These efforts have arisen from a number of human desires including, but not limited to, the desire to preserve animal species in numerical decline, to breed animals by in vitro fertilization techniques to increase genetic diversity and to overcome infertility problems, and to clone animals with high economic potential. With the growing interest in oocyte preservation, there has become an increasing awareness that current biological preservation techniques are less than adequate to preserve the oocytes of many animals species. For example, it is known that cattle oocytes are very sensitive to low temperatures. Despite the efforts of numerous research groups (See review by Palasz et al., *Biotechnol. Adv.* 14: 127–149 (1996)) cattle oocyte preservation remains a difficult task. Only a limited number of publications reported blastocyst and subsequent calf development from cryopreserved oocytes and the results remain inefficient (Fuku et al., *Cryobiology* 29: 485–492 (1992); Hamano et al., *Theriogenology* 38: 1085–1090 (1992); Otoi et al., *Theriogenology* 38: 711–719 (1992); Otoi et al., *J. Reprod. Dev.* 41: 361–366 (1995); Suzuki et al., *Cryobiology* 33: 515–524 (1996); Kubota et al., *Mol. Reprod. Dev.* 51: 281–286 (1998); Vajta et al., *Mol. Reprod. Dev.* 51: 53–58 (1998)).

It has been reported that the fertilization process can be compromised by the effect of cryoprotectants. A number of reports state that elevated concentrations of presently available cryoprotectants will have high toxicity with respect to oocytes and a negative effect on the subsequent development of oocytes and embryos (See, e.g., Martino et al., *Mol. Reprod Der.* 45: 503–512 (1996); Palasz et al., *Biotechnology Advances* 14: 127–149 (1996); Parks et al., *Theriogenology* 37: 59–73 (1992); Schellander et al., *Theriogenology* 42: 909–915 (1994); Vajta et al., *Embryo Transfer Newsletter* 15:12–18 (1997)). There are also reports of oocyte toxicity related to the cooling of cryopreservation (Parks et al., *Theriogenology* 37: 59–73 (1992)). For example, exposure to low temperature is known to result in de-polymerization of the meiotic spindle (Parks et al., *Theriogenology* 37: 59–73 (1992); Peura et al., *Theriogenology* 51: 211 (1999) (abstr.)). Previous experiments with frozen/thawed matured oocytes showed a significant reduction of enucleation rates when compared to fresh oocytes (Kubota et al., *Mol. Reprod. Dev.* 51: 281–286 (1998)).

Efforts today have centered on improving the survival rates of stored oocytes by improving cryopreservation techniques. According to Martino et al. (Martino et al., *Biol. Reprod.* 54: 1059–1069 (1996)), such efforts have focused on comparing different cryoprotectants (Otoi et al., *Theriogenology* 40: 801–807 (1993); Dinnyes et al., *Cryobiology* 31: 569–570 (1994)) and different freezing regimens (Lira et al., *Theriogenology* 35: 1225–1235 (1991)); or related vitrification methods (Otoi et al., *Theriogenology* 40: 801–807 (1993); Otoi et al., *Cryobiology* 37: 77–85 (1998)).

By "cryopreservation" it is meant the storage of biological materials at below the freezing point of water such that the material does not decompose. By "vitrification" it is meant a process of cooling biological material, employing cryoprotectants (chemicals that protect water from freezing) to inhibit the formation of ice in the cooling process, to a temperature about −100 degrees Celsius or lower, such that the solution containing the biological material reaches its glass transition temperature, that is the molecules cease to move relative to each other. It is recognized in the art that ice formation is damaging to biological material, in that it forces the material into shrinking pockets of residual unfrozen solution. As cooling continues, more than eighty percent of tissue volume can become converted to ice, and cells crushed beyond recovery. During vitrification, liquid water molecules maintain their natural random arrangements during deep cooling. There is no disturbance of other chemicals or cell components. Successful vitrification techniques make use of supercooling, that is cooling below the freezing point of the cryoprotection solution without freezing. Cryoprotectants are typically toxic to cells at high concentrations. Rapid freezing is believed to work by decreasing the concentration of cryoprotectant necessary to protect against ice crystal formation, thereby preserving the tissue at non-toxic concentrations of cryoprotectants.

It is believed that one of the bottlenecks of vitrification technology is the "insufficient" cooling rate of oocytes in current vitrification schemes (Vajta et al., *Embryo Transfer Newsletter* 15: 12–18 (1997)). In order to overcome this problem, several methods have been proposed which use very small amounts of solution So-called "minimum drop vitrification" systems have allowed breakthrough results with bovine and porcine oocyte cryopreservation (See, e.g., Arav A., *Vitrification of oocyte and embryos*, In: Lauria A, Gandolfi F (eds.), *New trends in embrvo transfer*, Cambridge, England: Portland Press, 255–264 (1992)). In "minimum drop vitrification" small amounts of solution are placed on a special cryo-stage which is cooled down quickly. This method, unfortunately, has not been found by the art to be convenient for preserving large numbers of oocytes.

Other vitrification techniques have been reported. Methods utilizing few microliters of vitrification solution loaded into glass capillaries (Dinnyes et al., *Cryobiology* 31: 569–570 (1994)), or into open pulled plastic straws (Vajta et al., *Mol. Reprod. Dev.* 51: 53–58 (1998)) and then plunged quickly into liquid $N_2$ were successfully tested for bovine oocyte vitrification. Similarly vitrification success was achieved by plunging oocyte-containing vitrification solutions with a small loop (Lane et al., *Theriogenology* 51: 167 (1999) (abstr.)). However, such techniques have not been found highly efficient presumably because plunging a warm object into liquid $N_2$ results in the boiling of the liquid and for a short time creates an isolating layer of $N_2$ vapor around the object.

In order to reduce the possibility of an isolating layer of vapor interfering with efficient vitrification, it has been proposed that oocyte-containing vitrification solution be dropped directly into liquid $N_2$. Such technique has been reported to be more effective than prior art vitrification techniques. (Riha et al., *Zivoc. Vir.* 36: 113–120 (1991); Papis et al., *Theriogenology* 51: 173 (1999) (abstr.); Yang et al., *Theriogenology* 51: 178 (1999) (abstr.)), presumably by eliminating the insulation effect of the vapor. However, such technique suffers from the problem of vitrified oocyte retrieval.

Some groups have reported improved success of the cryopreservation of biological materials by using metal surfaces cooled down with the aid of liquid $N_2$. Such metal surfaces are asserted to provide a more efficient heat transfer and to increase further the cooling rates than the cryo-stages used in minimum drop vitrification. Drosophila embryos were successfully preserved by placing them in a metal grid on a cold metal surface (Steponkus et al., *Nature* 345: 170–172 (1990)). Again, presently available techniques employing cooled metal surfaces have not been found convenient for preserving large numbers of oocytes.

Currently, as a consequence of the limited survival of preserved oocytes, and the cumbersome techniques available, in vitro embryo production and nuclear transfer experiments in cattle rely on freshly collected oocytes. This is a major limitation to numerous research teams and presents an obstacle to efficient planning and organizing of experiments.

There is a need therefore for improved biological material preservation methods, particularly those useful for preserving oocytes and other fragile cells. The method should permit the sterile handling of the biological material and preserve biological activity and viability for long periods of time.

SUMMARY OF THE INVENTION

The present invention provides a novel method for cryopreserving biological materials, particularly oocytes, embryos, and other cellular materials. It has been discovered by the present inventors that cryopreservation of biological materials may be accomplished by incorporating the material into very small droplets of a fluid comprising a vitrification solution and then directly contacting the biological material-containing vitrification fluid with a very cold surface having good heat conductivity. All of these elements together result in a very high cooling rate.

The presently described invention provides extremely good results with respect to oocyte preservation, a problem that has plagued the prior art as discussed above. Improved preservation of oocytes provides both improved survival of the oocyte and a very improved ability to support the development of nuclear transfer embryos. The level of this improvement is clearly unanticipated, representing a ten fold increase in efficiency as compared to earlier reports (See, e.g., Peura et al., *Theriogenology* 51: 211 (1999) (abstr.))

The method of the present invention, referred to as the "solid surface vitrification" or "SSV" method, combines the advantages of the containerless vitrification in microdrops techniques, and the increased heat exchange of the cold metal surface techniques, described above. Furthermore, the clean metal surface facilitates the sterile handling of the droplets.

The solid surface vitrification method of the present invention may be used to cryopreserve various kind of living cells and tissues, including, but not limited to, cells and tissues from vertebrate and non-vertebrate animal species, as well as, plants. The method can be used with various combinations of cryoprotectant solutions, as known to those of ordinary skill in the art, when the concentration of cryoprotectant in the solution allows the vitrification process to take place, preferably without adversely affecting the biological activity of the biological material.

In one embodiment of the present invention, there is provided a method for the vitrification of biological materials, said method comprising the steps of: (1) suspending the biological material in a cryoprotective equilibration medium, having a concentration of cryoprotectant(s) below that sufficient to protect against ice formation to the glass transition temperature of the cryoprotective equilibration medium; (2) rinsing the equilibrated biological material with a vitrification solution, the vitrification medium having a concentration of cryoprotectant(s) sufficient to protect against ice formation to the glass transition temperature of the vitrification medium; and (3) dropping the vitrification solution-rinsed biological material in microdroplets of vitrification solution onto a solid surface with good heat conductivity having been previous cooled down to about $-150°$ C. to about $-180°$ C. By "good heat conductivity" it is meant a heat conductivity about that of a metal. A preferred thermal conductivity at $20°$ C. is >about 10 W/(m-k), more preferably >about 25 W/(m-k), more preferably >about 40 W/(m-k), and yet more preferably >about 55 W/(m-k). By "microdroplet" it is meant a droplet containing 10 µl or less of solution. A preferred microdroplet volume is 4 µl or less of solution, more preferably 3 µl or less of solution, and yet more preferably 1 µl or less of solution.

In another embodiment of the present invention there is provided an improved method for cryopreserving biological material suspended in a vitrification solution, wherein the improvement comprises contacting microdroplets of the vitrification solution containing the biological material with a solid surface having a temperature of about $-150°$ C. to about $-180°$ C., said surface having a good heat conductivity. In another embodiment of the present invention there is provided an improved method for cryopreserving biological material suspended in a vitrification solution, wherein the improvement comprises contacting microdroplets of the vitrification solution containing the biological material with a solid surface having a temperature of about $-150°$ C. to about $-180°$ C., said surface having a thermal conductivity at $20°$ C. of >about 10 W/(m-k).

Samples that are cryopreserved by the present vitrification technique can be warmed without significant deleterious effect of biological activity by placing the vitrified droplets directly into warm (about $39°$ C.) buffered solution (0.3 M prehalose solution) for several minutes (about 3 minutes) with or without added sugars or other osmotically active agents.

The present invention may in particular be used by researchers to compensate for the obstacles faced through fluctuations in oocyte availability and seasonal quality variations. Furthermore, preservation of endangered animals and farm animal breeds could be facilitated by the successful cryostorage of such oocytes. The present invention improves upon the existing technology in at least the following aspects: (1) it eliminates the isolating effect of the container's walls used in most of the existing techniques; (2) the direct contact with a solid surface eliminates the isolating effect of the low temperature gas around samples plunged into liquid low temperature gas, e.g., $N_2$, and provides a better heat transfer and subsequently a more efficient vitrification. The efficacy of the present invention in preserving oocytes is higher than any other documented method, and it is believed to be cheaper to perform.

In a preferred embodiment, vitrified/thawed oocytes can be used successfully as recipients for somatic-cell nuclear transfer with high blastocyst development. This finding has important implications for nuclear transfer research and practice.

Previously, Lim et al. (Lim et al., *Theriogenology* 35: 1225–1235 (1991)) obtained blastocyst stage embryos following IVF of frozen-thawed matured bovine oocytes. Since then several teams have investigated the possibility of cryopreservation for bovine oocytes. Oocyte survival and subsequent blastocyst development, however, remained low ranging from 0 to 10% (Fuku et al., *Cryobiology* 29: 485–492 (1992); Otoi et al., *Theriogenology* 38: 711–719 (1992); Otoi et al.,*J. Reprod. Dev.* 41: 361–366 (1995); Otoi et al., *Theriogenology* 40: 801–807 (1993); Dinnyes et al., *Cryobiology* 31: 569–570 (1994); Otoi et al., *Cryobiology* 37: 77–85 (1998); Lim et al., *Theriogenology* 37: 351–361 (1992); Schellander et al., *Theriogenology* 42: 909–915 (1994)). Few limited studies (Hamano et al., *Theriogenology* 38: 1085–1090 (1992); Otoi et al., *Theriogenology* 38: 711–719 (1992); Suzuki et al., *Cryobiology* 33: 515–524 (1996); Kubota et al., *Mol. Reprod. Dev.* 51: 281–286 (1998); Vajta et al., *Mol. Reprod. Dev.* 51: 53–58 (1998)) have resulted in pregnancies or births following transfer of embryos originating from frozen-thawed bovine oocytes. Encouragingly, recent development of vitrification methods substantially increased the success rates, reportedly up to 25% (Vajta et al., *Mol. Reprod. Dev.* 51: 53–58 (1998)); and 30% (Papis et al., *Theriogenology* 51: 173 (1999) (abstr.)) blastocysts derived from IVF of vitrified matured bovine oocytes. These improved success rates were believed to be attributed to the increased cooling rate during oocyte vitrification (Vajta et al., *Embryo Transfer Newsletter* 15: 12–18 (1997)). Following the present methods of the present invention, however, following cryopreservation the rate of morphologically intact oocytes was as high as 86%, far exceeding that previously obtained.

In a preferred embodiment of the present invention there is provided an improved method for cryopreserving oocytes suspended in a vitrification solution, wherein the improvement comprises contacting microdroplets of the vitrification solution containing the oocytes with a solid surface having a temperature of about –150° C. to about –180° C., said surface having a good heat conductivity. In another embodiment of the present invention there is provided an improved method for cryopreserving oocytes suspended in a vitrification solution, wherein the improvement comprises contacting microdroplets of the vitrification solution containing the oocytes with a solid surface having a temperature of about –150° C. to about –180° C., said surface having a thermal conductivity at 20oC of >than about 10 W/(m-k).

In another preferred embodiment of the present invention, there is provided a method for the vitrification of oocytes, said method comprising the steps of: (1) suspending the biological material in a cryoprotective equilibration medium, having a concentration of cryoprotectant(s) below that sufficient to protect against ice formation to the glass transition temperature of the cryoprotective equilibration medium; (2) rinsing the equilibrated oocytes with a vitrification solution, the vitrification medium having a concentration of cryoprotectant(s) sufficient to protect against ice formation to the glass transition temperature of the vitrification medium; and (3) dropping the vitrification solution-rinsed oocytes in microdroplets of vitrification solution onto a solid surface with good heat conductivity having been previous cooled down to about –150° C. to about –180° C. The oocytes used for vitrification may be partially (except for the 3–5 inner layers) or fully stripped of their cumulus cells prior to placing the oocytes in the cryopreservation solution. The thawed vitrified oocytes can be used as required by the artisan, as for example, in nuclear transfer cloning techniques.

In another embodiment of the present invention there is provided a method for increasing blastocyst development rates. It has been discovered by the present inventors that parthenogenetic development of vitrified oocytes in a defined KSOM plus BSA culture system may be significantly improved by co-culturing with cumulus-cells. It has been discovered by the present inventors that parthenogenetic development using such technique can increase blastocyst development to 32%.

DETAILED DESCRIPTION OF THE INVENTION

Figure 1:
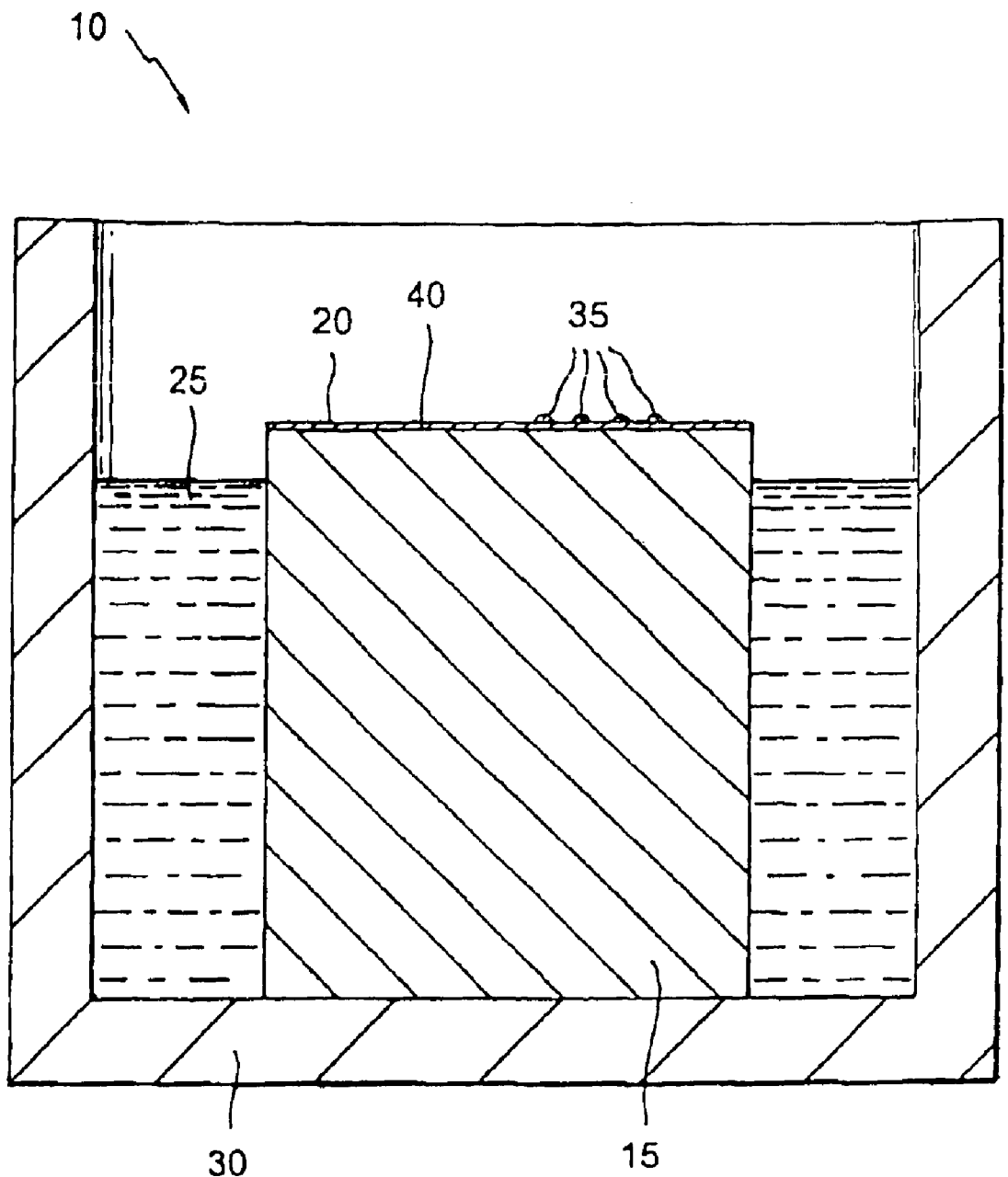
FIG. 1 illustrates a cross-sectional view of a solid surface vitrification (SSV) device of the present invention.

The present invention discloses a new method for cryopreserving biological samples, in particular cellular material, such that the biological functionality of the material is preserved after warming. In particular, the present invention discloses a method for vitrifying and thawing oocytes and embryos. Further disclosed is a method for somatic-nuclear transfer into previously vitrified oocytes.

Cryopreservation of mammalian oocytes by the present invention may provides a steady source of materials for nuclear transfer and in vitro embryo production. There is provided by the present invention an effective vitrification protocol to cryopreserve bovine oocytes for research and practice of parthenogenetic activation, in vitro fertilization and nuclear transfer.

In a preferred embodiment of the present invention, in vitro matured bovine oocytes were placed in 4% ethylene glycol (EG) in TCM 199 plus 20% fetal bovine serum (FBS) at 39° C. for 12–15 min, and then transferred to vitrification solution (35% EG, 5% polyvinyl-pyrrolidone (PVP), 0.4 M trehalose in TCM 199 and 20% FBS). Oocytes were vitrified in microdrops on a pre-cooled (–150° C.) metal surface (solid surface vitrification or SSV). The vitrified microdrops were stored in liquid $N_2$ and thawed immediately or following storage for 2–3 weeks or longer as needed.

It has been seen by the present inventors that the immediate survival of vitrified/thawed oocytes according to the present invention varies between 77% and 86% for treated oocytes cultured in KSOM containing BSA or FBS for 9 to 10 days. For nuclear transfer it was noted that vitrified oocytes supported embryonic development equally well as fresh oocytes.

While not limiting themselves to any particular theory, the present inventors have opined that the relatively high rates of cryo-survival, and embryo development following vitrification of bovine oocytes can be contributed to several factors. The solid metal surface vitrification method used likely achieves a high cooling rate by the combination of microdrops and improved heat exchange by direct contact with a metal surface. The warming of the oocytes is equally as fast by directly dropping the vitrified sample into a warm solution.

The high success rates may also be attributable to some procedural modifications, some of which were made based on recent development reported by others (Vajta et al., *Mol. Reprod. Dev.* 51: 53–58 (1998); Martino et al., *Biol. Reprod.* 54: 1059–1069 (1996); Dinnyes et al., *Cryobiology* 31: 569–570 (1994); Otoi et al., *Cryobiology* 37: 77–85 (1998); Papis et al., *Theriogenology* 51: 173 (1999) (abstr.); Vincent et al., *Cryo-Lett.* 8: 356–361 (1988)). Specifically, the present invention handled oocytes in solutions at or close to physiological temperatures followed by quick cooling and warming to/from vitrification temperature in order to "outrun" the chilling damages.

Bovine oocytes are known to be very sensitive to chilling (Aman et al., *Biol. Reprod.* 50: 103–110 (1994); Martino et al., *Mol. Reprod. Dev.* 45: 503–512 (1996); Parks et al., *Theriogenology* 37: 59–73 (1992); and immature oocytes (GV stage) have been reported to be more sensitive than matured oocytes (Fuku et al., *Cryobiology* 29: 485–492 (1992); Lim et al. *Theriogenology* 37: 351–361 (1992)). Parks and Ruffing (Parks et al., *Theriogenology* 37; 59–73 (1999)) and Aman and Parks (Aman et al., *Biol. Reprod.* 50: 103–110 (1994)) have reported damage of the metaphase II spindles following cooling to temperatures between 25° C. and 4° C. for only 1 min. Vitrification techniques, such as that described in the present invention, may allow reduction of the time while the oocytes are exposed to critical chilling temperatures compared to freezing methods and thus might be superior to the conventional freezing method for oocytes and in vitro produced embryos (Palasz et al., *Biotechnol. Adv.* 14: 127–149 (1996); Martino et al., *Biol. Reprod.* 54: 1059–1069 (1996); Vajta et al., *Embryo Transfer Newsletter* 15: 12–18 (1997)).

In a preferred embodiment of the present invention, cryopreservation of cattle oocytes or embryos is performed as follows:

Oocytes or embryos are suspended in an equilibration medium consisting of 4% (v/v) ethylene glycol or other intracellular cryoprotective agent in moderate concentration, in a base medium (TCM 199 or similar solutions) supplemented with 20% fetal bovine serum, or bovine serum albumin, or any other macromolecules with surfactant effects at room temperature, or higher, physiological temperatures (39° C. for example) for several minutes. Following this equilibration period, groups of oocytes or embryos are rinsed at least two times in small drops of vitrification solution consisting of 35% ethylene glycol (or other intracellular cryoprotectants in high concentration), 5% polyvinyl-pyrolidone (or other macromolecules), 0.4 M trehalose (or other sugars) in base medium and 20% fetal bovine serum, or other surfactant compounds, as described above, for a few seconds and dropped on the surface of a steel cube, or other solid surface with good heat conductivity, which is cooled down to around −150° C. to −180° C. or similar subzero temperatures by partially immersing it into liquid or solid nitrogen or into other cooling agents. It is preferred that the drop size be about 4 $\mu$l or smaller, more preferably 3 $\mu$l or smaller, and yet more preferably 2 $\mu$l or smaller, and yet more preferably 1 $\mu$l or smaller, which allows instantaneous vitrification. The vitrified droplets can be moved with a nitrogen-cooled forceps or other tool into 1-ml cryovials or other suitable containers.

FIG. 1 illustrates a cross-sectional view of a solid surface vitrification device (10) useful for cryopreserving using the present disclosure. A metal cube (15) is covered with a foil (20), such as a aluminum foil, and partially submerged into liquid $N_2$ (25) held by container (30). Microdrops of vitrification solution (35), containing the biological sample, such as an oocyte, are dropped on the cold upper surface (40) of metal cube (15) and vitrified instantaneously.

The present inventors have found that the presence of a few cumulus-cell layers surrounding the oocytes prior to vitrification had no harmful effect on the cleavage and developmental rates following parthenogenetic activation. The presence of the cumulus cells can be an important factor to achieving high fertilization rates following IVF, although nuclear transfer experiments require the removal of the cumulus cells before enucleation. The vitrified/thawed oocytes seemed to be more fragile, and care must be taken for the removal of the cumulus cells prior to nuclear transfer manipulation.

While the parthenogenetic activation of vitrified oocytes may be reduced compared to the controls, parthenogenetic activation may be significantly improved by changing the culture conditions. For example, the parthenogenetic development of vitrified oocytes was further increased (up to 32% blastocyst) by using cumulus-cell co-culture with KSOM plus FBS media.

Development of in vitro fertilized oocytes may also be reduced by vitrification if temperature fluctuations occur during storage in the gas-phase of the nitrogen container, or during handling before/after storage. Liquid-phase storage may be used to reduce such effects. Studies suggest that any reduced developmental competence is not due to impaired fertilization (in accord, Martino et al., *Theriogenology* 37: 59–73 (1992) and Kubota et al., *Mol. Reprod. Dev.* 51: 281–286 (1998), studies involving cattle; but see, in contrast, Ito et al., *Mol. Reprod. Dev.* 54: 81–85 (1999) wherein freezing was seen to result in a failure of the zona block to polyspermy in mice).

Nuclear transfer experiments normally utilize recipient cytoplasts from in vivo or in vitro matured oocytes. Previously, the present inventors have demonstrated that frozen-thawed oocytes can be used for nuclear transfer with embryo-derived blastomeres, and calves were produced by this procedure (Kubota et al., *Mol. Reprod. Dev.* 51: 281–286 (1998)). The present cryopreservation procedure for bovine oocytes benefits nuclear transfer research and practice significantly because it eliminates seasonal fluctuations, and the dependence on timing of slaughtering and oocyte shipping.

Following the presently disclosed methods a vast majority of oocytes (about 94%) will survive the vitrification process (a rate that is not different from controls), a rate which is much higher than that achieved in earlier freezing experiments by Ito et al., *Mol. Reprod. Dev.* 54: 81–85 (1999) (62%) and Kubota et al., *Mol. Reprod. Dev.* 51: 281–286 (1998) (74%). The surviving oocytes can effectively be used in nuclear transfer procedures, with no reduction detected in the enucleation rates for the vitrified-thawed oocytes. Vitrification has been hypothesized beneficial by reducing the exposure time to the critical temperature zone, as cooling the oocytes instantaneously into a vitrified state allows no time for spindle depolymerization (Vajta et al., *Mol. Reprod. Dev.* 51: 53–58 (1998); Martino et al., *Biol. Reprod.* 54: 1059–1069 (1996)).

The present invention may render high fusion, cleavage and blastocyst development rates, comparable to the rates seen with fresh controls. To the present inventors' knowledge, the present invention is the first to suggest the use of cryopreserved oocytes as recipients for somatic-cell nuclear donors with promising blastocyst development rate. Earlier attempts for open-pulled straw vitrification of cytoplasts and use of them in blastomere-nuclear transfer experiments resulted in a significant reduction in blastocyst development rates compared to fresh recipient cytoplasts (9.1% vs. 34.5%, respectively) (Peura et al., *Theriogenology* 51: 211 (abstract) (1999)).

In short, the cryopreservation methods of the present invention are capable of preserving oocytes such that a high percentage will survive thawing, and demonstrate high cleavage rates upon activation. Such oocytes are capable of development into morphological good quality blastocysts following parthenogenetic activation, in vitro fertilization, and nuclear transfer. Similar rates of development are observed among the somatic-cell nuclear transferred embryos using vitrified-thawed MII oocytes vs. control fresh oocytes as nuclear recipients. The nuclear transferred embryos produced may be used to produce progeny.

In order to more clearly describe the subject invention, the following examples are set forth along with the common materials and methods used to undertake the same. The examples below are non-limiting and are merely representative of various aspects and features of the present invention.

REPRESENTATIVE EXAMPLES

Materials and Methods

1. Source of Oocytes

Bovine ovaries were collected from slaughterhouse ovaries and in maturation medium at about 37° C. to 39° C. within 19 hours of start of maturation. Matured cumulus oocyte complexes were selected based on their morphology. They were then cryopreserved at 20–23 h post-maturation for nuclear transfer, parthenogenetic activation and in vitro fertilization assays.

2. Vitrification and Thawing

Matured oocytes were partially (except for the 3–5 inner layers), or fully stripped of their cumulus cells by a short exposure to 0.1% hyaluronidase (Sigma, St Louis, Mo., Cat. No. H3506) followed by pipetting. Oocytes were washed three times in TCM 199 with Earle's salt (Gibco, Paisley, Scotland, Cat. No. 041 01150H) supplemented with 20% (v/v) fetal bovine serum (FBS, Gibco, Hyclone, Cat No. 10099-41) and then suspended in an equilibration medium consisting of 4% (v/v) ethylene glycol (EG, Sigma, Cat. No. E9129) in TCM 199 supplemented with 20% FBS at 39° C. for 12–15 min. Following equilibration, groups of 5 to 10 oocytes were rinsed three times in small drops of vitrification solution consisting of 35% EG, 5% polyvinyl-pyrrolidone (Sigma, Cat. No. P0930), 0.4 M trehalose (Sigma, Cat. No. T0167) in TCM 199 and 20% FBS, for 25–30 seconds, and placed into trehalose solution (solution toxicity control), or dropped on the surface of a steel cube, which was covered with aluminum foil and cooled down to around −150° C. to −180° C. by partially immersing it into liquid $N_2$.

The drops placed on the metal surface varied in size between 1 and 2 $\mu l$, and were vitrified instantaneously. The vitrified droplets were moved with a nitrogen-cooled forceps into 1-ml cryovials for long term storage (2–3 weeks), or thawed immediately by dropping them into 39° C. 0.3 M trehalose solution for 3 minutes. Oocyte survival was then evaluated based on the integrity of the oocyte membrane and the zona pellucida. The surviving vitrified-thawed oocytes were subjected to activation, in vitro fertilization, or nuclear transfer experiments.

3. Parthenogenetic Activation of Oocytes

The methods described by Susko-Parrish et al. (Susko-Parrish et al., *Dev. Biol.* 166: 729–739 (1994)) was modified and employed for parthenogenetic activation After a total of 22 hours, in in vitro maturation culture ("IVM") (30 min additional culture for MII oocytes after thawing), oocytes were fully denuded of cumulus cells by pipetting. Oocytes were activated by a 5-minute exposure to Ca-ionophore A23187 (Sigma, Cat. No. C7522) at room temperature followed by culture in 2.5 mM 6-dimethylaminopurin (DMAP, Sigma Cat. No. D2629) for 3.5 hours (Liu et al., *Mol. Reprod. Dev.* 49: 298–307 (1998)). Following washing the treated oocytes were cultured in KSOM (Liu et al., *Mol. Reprod. Dev.* 49: 298–307 (1998)) plus 0.1% BSA (fraction V, Sigma, A941B) for an additional 48 hours. The culture environment consisted of 5% $CO_2$ in humidified air, or 5% $O_2$, 5% $CO_2$, and 90% $N_2$ at 39° C. Morphological survival as well as cleavage rates were recorded. All cleaved embryos were cultured further in KSOM medium supplemented with 1% BSA for 7 days.

4. In Vitro Fertilization and Culture

Vitrified-thawed oocytes and non-vitrified fresh control oocytes were fertilized with frozen-thawed bull semen from a single ejaculate. Frozen-thawed sperm were washed twice by centrifugation in modified Brackett-Oliphant (Liu et al., *Mol. Reprod. Dev.* 49: 298–307 (1998)) medium supplemented with 10 mM caffeine and 4 mg/ml BSA and then re-suspended in the fertilization medium (m-BO medium supplemented with 10 g$\mu$l/ml heparin and 4 mg/ml BSA). Sperm concentration was adjusted to $1 \times 10^7$/ml, and then about 25 oocytes were added to 100 $\mu l$ fertilization-medium droplets. After 6-hours sperm-oocyte incubation, the oocytes were washed and cultured in KSOM medium supplemented with 0.1% BSA for 48 hours at 39° C., in a humidified atmosphere of 5% $O_2$, 5% $CO_2$, and 90% $N_2$. After 48-hours in culture, the IVF eggs were freed of cumulus cells by pipetting and cleavage rates were recorded. The cleaved embryos were cultured further in KSOM supplemented with 1% BSA in an atmosphere of 5% $O_2$, 5% $CO_2$, and 90% $N_2$ for another 7 days. Medium was changed every two days throughout the culture period.

5. Nuclear Transfer

After IVM for 20 hours, vitrified-thawed oocytes in metaphase II as well as fresh control oocytes were denuded from cumulus cells and selected by the presence of the first polar body. Enucleation was achieved by piercing the zona pellucida with a glass needle and pushing out the polar body and the surrounding cytoplasm (Kubota et al., *Mol. Reprod. Dev.;* 51: 281–286 (1998)). Successful enucleation was confirmed by Hoechst 33342 fluorescent staining of the pushed-out karyoplasts. Confluent fibroblast cells at passage 29–31, serum starved for 4 to 6 days, were then transferred individually into the perivitelline space of the enucleated oocyte (cytoplast). Cytoplast-fibroblast complexes derived from the vitrified-thawed oocytes vs. fresh control oocytes were then fused and activated with two DC-pulses (50 V/mm, 10 $\mu$-sec, 1 sec apart) in Zimmerman cell fusion medium (Zimmermann et al., *J. Membrane. Biol.* 67: 165–182 (1982)) in a 1-mm gap electrofusion chamber by a BTX200 Electro Cell Manipulator (San Diego, Calif.). They were then cultured in KSOM medium supplemented with 10 $\mu$g/ml cycloheximide (Sigma, Cat. No. C6255) and 2.5 $\mu$g/ml cytochalasin-D (Sigma, Cat. No. C8273) and 0.1% BSA for 1 hour, and for an additional 4 hours in KSOM medium with cycloheximide (10 g$\mu$/ml) and BSA without cytochalasin-D. After activation, embryos were cultured further in KSOM and 0.1% BSA medium for 48 hours in an atmosphere of 5% $O_2$, 5% $CO_2$, and 90% $N_2$. The cleaved embryos were then selected and cultured further for 7 days in KSOM supplemented with 5% FBS on cumulus-cell monolayers in an atmosphere of 5% $CO_2$ in air. Medium was changed every two days throughout the culture period. Non-cleaved eggs were stained to check the rate of non-fused cytoplast-fibroblast complexes. Morphologically high quality nuclear transfer blastocysts were vitrified with the VS3a method (Rall et al., J. Reprod. Fertil. 101: 681–688 (1994); Dinnyes et al., *Mol. Reprod. Der.* 53: 318–324 (1999)) and stored for future embryo transfer purposes. As a control for the oocyte cryopreservation process, some oocytes from the vitrified-thawed groups used for nuclear transfer experiments were activated as described earlier (Ca-ionophore and DMAP), and cultured the same way as the nuclear transfer embryos.

6. Statistics

All experiments were repeated at least three times. Development of oocytes was evaluated and treatments were compared using Chi-square analyses.

Experiment 1

Parthenogenetic Development of Vitrified Oocytes

Protocol:

Matured oocytes were vitrified-thawed and activated parthenogenetically as described above. The toxicity of the vitrification solution, without cooling was tested and the effect of the presence vs. removal of the cumulus cells prior to cryopreservation was compared. Furthermore, culture of activated oocytes in high (20%) vs. low (5%) $O_2$-content atmosphere was tested in two separate trials.

Results:

Results of the parthenogenetic activation experiments are presented in Table 1 and 2. Table 1 presents the results of parthenogenetic development of matured oocytes vitrified with vs. without cumulus cells and cultured in an atmosphere of 5% $CO_2$ in air.

TABLE 1

Parthenogenetic development of vitrified/thawed matured bovine oocytes cultured under 5% $CO_2$ in air

| Oocytes treated | n | % oocytes survived | % cleaved Day 2[a] | % blastocyst (BL)[a] | | | % expanded or hatched BL[a] |
|---|---|---|---|---|---|---|---|
| | | | | Day 7 | Day 8 | Day 9 | |
| Vitrified + cumulus | 42 | 86[b] | 64[bc] | 0[b] | 8[b] | 11[b] | 8[b] |
| Vitrified − cumulus | 68 | 79[b] | 52[b] | 6[b] | 6[b] | 6[b] | 3[b] |
| Non-vitrified | 47 | 100[c] | 81[c] | 13[b] | 17[b] | 17[b] | 15[b] |

[a]Based on surviving oocytes
[b,c]Groups with different superscripts within the same columns are significantly different (P < 0.05)

Table 2 summarizes the developmental data following similar treatments but with embryos cultured in a reduced $O_2$-content (5%) atmosphere. Immediate survival of the oocytes (i.e. no lysis after thawing through the start of the culture period) varied between 77% and 86%, but were not different between oocytes with or without cumulus prior to vitrification (P>0.05).

TABLE 2

Parthenogenetic development of vitrified/thawed matured bovine oocytes cultured under an atmosphere of 5% $O_2$, 5% $CO_2$, and 90% $N_2$

| Oocytes treated | n | % oocytes survived | % cleaved Day 2[a] | % blastocyst (BL)[a] | | | % expanded or hatched BL[a] |
|---|---|---|---|---|---|---|---|
| | | | | Day 7 | Day 8 | Day 9 | |
| Vitrified + cumulus | 127 | 77[b] | 56[b] | 11[bc] | 14[bc] | 17[bc] | 14[bc] |
| Vitrified − cumulus | 118 | 81[b] | 56[b] | 3[b] | 11[b] | 16[b] | 11[b] |
| Solution alone | 85 | 94[c] | 69[bc] | 16[cd] | 23[cd] | 30[cd] | 25[c] |
| Non-vitrified | 98 | 98[c] | 79[c] | 27[d] | 32[d] | 32[d] | 26[b] |

[a]Based on surviving oocytes
[b,c,d]Groups with different superscripts within the same columns are significantly different (P < 0.05)

When compared retrospectively, low $O_2$ atmosphere culture resulted in superior (P<0.05) blastocyst development compared to the high $O_2$ level tension (20%) treatment. In the high $O_2$ experiment, cleavage rates of activated non-frozen controls were significantly higher than those of the vitrified/thawed groups (P<0.05), but blastocyst development was not different (P>0.05). In the reduced $O_2$ experiment cleavage and blastocyst development of vitrified oocytes was lower than that of the controls (P<0.05), however, the solution treatment alone caused no reduction in those parameters (P>0.05). The development of oocytes vitrified with or without cumulus cells was not significantly different (P>0.05) regardless of the culture environment. The blastocyst formation from the vitrified and solution treatment groups appeared approximately 1 day later compared to that of the fresh controls. The rate of expanded and hatched blastocysts developing from vitrified oocytes was significantly lower than from the controls (P<0.05).

In the present study, toxicity test of the vitrification solution (Experiment 1) showed no reduction in cleavage and blastocyst development compared to that of the controls. Our earlier results showed that ethylene glycol has a relatively low toxicity for bovine oocytes (Dinnyes et al., Cryobiology 31: 569–570 (1994)), and the gradual equilibration in a low concentration cryoprotectant solution prior to vitrification was reported beneficial by others (Papis et al., Theriogenology 51: 173 (1999) (abstr.)). The use of a mixture of a relatively low molecular weight and high penetration-rate cryoprotectant (ethylene glycol), a viscosity-increasing compound (polyvinyl-pyrrolidon), and a membrane-protective sugar (trehalose) assured that even a short exposure to the solution would result in the vitrification of the oocytes. A similar mixture was used successfully for bovine embryo vitrification (Saha et al., Cryobiology 33: 291–299 (1996)). The very short exposure to high concentration of ethylene glycol before cooling and after thawing reduced its toxic effects. Moreover, toxic effects during thawing were minimized by the direct dilution method.

Experiment 2

In Vitro Development of Fertilized Vitrified/Thawed Oocytes

Protocol:

Vitrified-thawed oocytes were fertilized in vitro as described above. Based on the results from Experiment 1, cumulus was only partially removed prior to vitrification. The control oocytes were treated with hylauronidase, and their surrounding cumulus layers were similarly partially removed before fertilization. Vitrified oocytes were either immediately thawed, or stored in liquid nitrogen containers for several days or weeks. Fertilized zygotes were cultured further in low $O_2$-content atmosphere.

Results:

Development of in vitro fertilized fresh vs. vitrified/thawed oocytes is presented in Table 3. Immediate survival of the oocytes (85% vs. 93% for controls) was slightly reduced by vitrification. Cleavage rates of the surviving oocytes did not differ significantly (58% vs. 69%, P>0.05), however blastocyst development of vitrified oocytes was significantly lower than that of the controls (20% vs. 35%, P<0.05). Furthermore, prolonged storage of the oocytes resulted in a further, significant reduction in blastocyst development (11% vs. 20%, P<0.05). Development to expanded and hatched stages was not significantly reduced by vitrification (12% vs. 19%, P>0.05). Cryostorage of oocytes, however, negatively affected the hatching rate (6% vs. 19%, P<0.05).

Experiment 3

Development of Cloned Embryos with Vitrified/Thawed Oocytes

Protocol:

Vitrified-thawed oocytes were enucleated, and used as recipient cytoplasts for somatic-cell nuclear transfer. The enucleation, fusion, cleavage and blastocyst development rates of vitrified vs. fresh cytoplasts were compared. As a control group for the vitrification and culture system some of the vitrified-thawed oocytes were parthenogenetically activated and cultured further. The zygotes were cultured in a low $O_2$ atmosphere for the first two days, then for an additional 7 days co-cultured-with cumulus-cells in a high $O_2$-content atmosphere.

Results:

The data on nuclear transfer experiments using vitrified vs. fresh oocytes as a source of cytoplasts are presented in Table 4.

TABLE 3

In vitro development of vitrified/thawed matured bovine oocytes following in vitro fertilization

| Oocyte treatment | n | % oocytes survived | % cleaved on Day 2[a] | % blastocyst (BL)[a] | | | % expanded or hatched BL[a] |
|---|---|---|---|---|---|---|---|
| | | | | Day 7 | Day 8 | Day 9 | |
| Vitrified/thawed | 175 | 85[bc] | 58[b] | 15[c] | 19[c] | 20[c] | 12[bc] |
| Vitrified/stored/thawed | 258 | 81[b] | 62[b] | 6[b] | 11[b] | 11[b] | 6[b] |
| Non-vitrified | 98 | 98[cd] | 69[b] | 24[cd] | 33[d] | 35[d] | 19[c] |

[a]Based on surviving oocytes.
[b,c,d]Groups with different superscripts within the same columns are significantly different (P < 0.05).

TABLE 4

In vitro development of bovine nuclear transfer embryos from fresh or vitrified/thawed recipient oocytes

| Recipient oocyte/treatment | n | % fused | % cleaved on Day 2[a] | % blastocyst (BL)[a] | | | % expanded or hatched BL[a] |
|---|---|---|---|---|---|---|---|
| | | | | Day 7 | Day 8 | Day 9 | |
| Vitrified/NT | 106 | 62[b] | 85[b] | 17[b] | 21[b] | 27[b] | 20[bc] |
| Fresh/NT | 106 | 74[b] | 90[b] | 22[b] | 28[b] | 29[b] | 22[b] |
| Vitrified/activated | 109 | — | 56[c] | 25[b] | 30[b] | 32[b] | 10[c] |

[a]Based on fused embryos or activated oocytes
[b,c]Groups with different superscripts within the same columns are significantly different (P < 0.05).

Most of the oocytes (252/269, 94%) survived the vitrification process. Enucleation rate of fresh vs. vitrified oocytes did not differ (142/163, 87% vs. 127/139, 91%, respectively;

P>0.05). Fusion rates with cytoplasts obtained from fresh or vitrified/thawed oocytes (74% vs. 62%, P>0.05) did not differ. Subsequent development of embryos to cleavage (90% vs. 85%), blastocyst (29% vs. 27%) or hatched blastocyst stage (22% vs. 20%) did not differ statistically either (P>0.05). Cleavage rates of parthenogenetically activated vitrified/thawed oocytes (56%) was significantly lower than that of nuclear transfer embryos (P<0.01), however, development rates to blastocyst stage (32%) were not different. The rate of oocytes reaching expanded or hatched blastocyst stages following parthenogenetic activation was lower (10%) than after nuclear transfer.

While the invention has been described with respect to preferred embodiments, those skilled in the art will readily appreciate that various changes and/or modifications can be made to the invention without departing from the spirit or scope of the invention as defined by the appended claims. All documents cited herein are incorporated in their entirety herein.

What is claimed is:

1. A method for cryopreservation of bovine oocyte morphology and viability, comprising the steps:
    (a) suspending bovine oocytes in a medium comprising about 4% ethylene glycol and about 20% bovine serum for about 15 min at a temperature at or near physiological temperatures;
    (b) rinsing the oocytes for about 30 seconds in a solution comprising about 35% ethylene glycol, 0.4 M trehalose, 20% bovine serum and 5% polyvinylpyrrolidone;
    (c) vitrifying the oocytes in step (b) by quickly dropping microdroplets of the solution comprising the oocytes onto a solid surface that has a temperature between −150° C. and −180° C.; and
    (d) collecting frozen microdroplets that contain vitrified oocytes that maintain morphology and viability after thawing.

2. The method of claim 1 wherein cleavage rates of oocytes after thawing and in vitro fertilization are about 84% of cleavage rate of non-vitrified oocytes.

3. The method of claim 1 wherein blastocyst formation of oocytes after thawing and in vitro fertilization is about 58% of blastocyst formation of non-vitrified oocytes.

4. The method of claim 1 wherein the suspending is at near physiological temperature of 39° C.

5. The method of claim 1 wherein the rinsing is for about 25 seconds.

6. The method of claim 1 wherein the medium comprises a TCM 199 base medium.

7. The method of claim 1 further comprising storing the collected frozen microdroplets for at least three weeks prior to thawing.

8. The method of claim 1 further comprising partially or fully removing oocyte cumulus cells prior to step (a).

9. The method of claim 1 wherein the ethylene glycol raises the vitreous state glass transition temperature in the microdroplets sufficiently to inhibit ice formation.

10. The method of claim 1 further comprising thawing the vitrified oocyte microdroplets at a near physiological temperature for up to about 3 minutes.

11. The method of claim 10 further comprising fertilizing the thawed oocyte.

12. The method of claim 11 wherein the fertilized thawed oocyte is incubated to form an embryo.

13. The method of claim 12 wherein incubation is by cumulus cell-coculture with KSOM and fetal bovine serum media.

14. The method of claim 1 wherein the microdroplets have a volume of about 1–10 microliters.

15. The method of claim 14 wherein the microdroplets have a volume of 1 microliter.

16. The method of claim 10 further comprising enucleating the thawed oocytes for somatic cell nuclear transfer.

17. The method of claim 16 wherein the hatched blastocyst rate from nuclear transfer embryos is about 91% of rate of development from non-vitrified oocytes.

* * * * *